United States Patent
Fitzpatrick et al.

(10) Patent No.: US 8,231,636 B2
(45) Date of Patent: Jul. 31, 2012

(54) ANCHOR DRIVER WITH ASSURED SEATING

(75) Inventors: J. Michael Fitzpatrick, Nashville, TN (US); Robert F. Labadie, Nashville, TN (US); Jason E. Mitchell, Greenbrier, TN (US)

(73) Assignee: Vanderbilt University, Nashville, TN (US)

( * ) Notice: Subject to any disclaimer, the term of this patent is extended or adjusted under 35 U.S.C. 154(b) by 1019 days.

(21) Appl. No.: 12/185,434

(22) Filed: Aug. 4, 2008

(65) Prior Publication Data

US 2009/0036897 A1 Feb. 5, 2009

Related U.S. Application Data

(60) Provisional application No. 60/963,295, filed on Aug. 3, 2007.

(51) Int. Cl.
*A61B 17/58* (2006.01)
(52) U.S. Cl. ...................................................... 606/104
(58) Field of Classification Search .................. 606/104; 81/448, 449
See application file for complete search history.

(56) References Cited

U.S. PATENT DOCUMENTS

| | | | |
|---|---|---|---|
| 2,765,463 A * | 10/1956 | De Anguera | 227/139 |
| 2,923,191 A | 2/1960 | Fulop | |
| 2,940,488 A | 6/1960 | Riley, Jr. | |
| 5,354,292 A * | 10/1994 | Braeuer et al. | 606/1 |
| 5,398,861 A * | 3/1995 | Green | 227/175.1 |
| 5,411,523 A * | 5/1995 | Goble | 606/232 |
| 5,431,660 A | 7/1995 | Burke | |
| 5,741,268 A * | 4/1998 | Schutz | 606/104 |
| 7,243,581 B1 | 7/2007 | Gao | |

* cited by examiner

*Primary Examiner* — Nicholas Woodall
(74) *Attorney, Agent, or Firm* — Morris Manning & Martin, LLP; Tim Tingkang Xia, Esq.

(57) ABSTRACT

A surgical instrument for securing an anchor in a target area of the skull of a patient, wherein the anchor has a shaped surface, a top and a base. In one embodiment, the surgical instrument includes a driver having a first end, an opposite, second end, and a body portion defined therebetween forming a bore therein along a longitudinal axis, where the bore is configured to allow the anchor to be received therein, a first inner surface formed inside the bore proximate to the first end, wherein the first inner surface is formed with a shape that is complimentary to the shaped surface of the anchor, and a second inner surface formed inside the bore and between the first inner surface and the second end, wherein the second inner surface is formed with a shape that is different from that of the first inner surface.

6 Claims, 9 Drawing Sheets

ANCHOR DRIVER WITH ASSURED SEATING

CROSS-REFERENCE TO RELATED PATENT APPLICATION

This application claims the benefit, pursuant to 35 U.S.C. §119(e), of U.S. provisional Application Ser. No. 60/963,295, filed Aug. 3, 2007 entitled "Anchor Driver with Assured Seating" by J. Michael Fitzpatrick, Robert Labadie, and Jason E. Mitchell, the disclosure for which is hereby incorporated herein in its entirety by reference.

Some references, if any, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT OF FEDERALLY-SPONSORED RESEARCH

The present invention was made with Government support awarded by the National Institute on Deafness and Other Communication Disorders under contract No. 1R01DC008408-01A. The United States Government has certain rights to this invention pursuant to this grant.

FIELD OF THE INVENTION

The present invention generally relates to a surgical instrument, and more particularly relates to a surgical instrument for securing an anchor in a target area of the skull of a patient.

BACKGROUND OF THE INVENTION

Image-guided surgery technology has been clinically available since the mid-1980s. Analogous to global positioning systems (GPS), image-guided surgery facilitates intraoperative surgical navigation by linking preoperative radiographs to intraoperative anatomy. Central to the image-guided surgery process is registration: the linking of the radiographic images to the patient. To achieve high accuracy, the registration is based on fiducial markers that are identified both in the radiographs and on the patient. Fiducial markers need to be positioned by anchors, which have been used in other medical procedures as well.

A current system for image-guided surgery requires that self-tapping anchors be screwed into a patient's skull through an incision in the scalp. The fact that the anchor cannot be seen by a medical professional such as a surgeon during the screwing because of overlying scalp makes it difficult for the surgeon to know when and whether the anchor is fully seated against the skull. The anchor is placed into a driver that is inserted through the incision. The surgeon presses on the driver and begins to twist. If the surgeon twists too far, the threads that are tapped into the skull by the anchor will be stripped. If the surgeon does not twist far enough, the threads on the anchor will not be fully buried in the skull. In either case, the anchor will not be secure.

Therefore, a heretofore unaddressed need still exists in the art to address the aforementioned deficiencies and inadequacies.

SUMMARY OF THE INVENTION

Practicing the present invention may create an ideal situation where the base of the anchor is seated against the skull of a patient, at which point the anchor threads are fully buried and the threads in the skull are not stripped. This invention makes it possible for the surgeon to know when and whether this point it reached, such that proper seating is assured. In other words, the present invention provides for placement of the threaded component with pre-specified penetration into the bone surface of the patient.

The term "patient" as used herein encompasses, in addition to a living human subject, a living animal subject or cadaver, a human cadaver, or other living subjects. The present invention, in one aspect, relates to a surgical instrument for securing an anchor in a target area of the skull of a patient, where the anchor has a shaped surface, a top, and a base. In one embodiment, the surgical instrument has a driver with a first end, an opposite, second end, and a body portion defined between the first end and second end. The body portion has a bore inside, along a longitudinal axis, where the bore is configured to allow the anchor to be received inside. A first inner surface is formed inside the bore proximate to the first end, with a shape that is complimentary to the shaped surface of the anchor. A second inner surface, having a shape that is different from the shape of the first inner surface, is also formed inside the bore, between the first inner surface and the second end.

In one embodiment, the shaped surface of the anchor is cross-sectionally hexagonal, the first inner surface is cross-sectionally hexagonal, and the second inner surface is cross-sectionally cylindrical. The first inner surface is dimensioned to engage the shaped surface of the anchor, and the second inner surface is dimensioned to allow the anchor to slide inside the bore. In operation, as the driver is twisted, the anchor is driven into the skull to a depth at which the base of the anchor is aligned with the second end of the driver and is seated on the surface of the skull, while the top of the anchor is within the second inner surface of the driver. In one embodiment, the depth is adjustable. At least one of the first inner surface and second inner surface is dimensioned to allow the depth to be adjustable. In another aspect, the present invention relates to a surgical instrument for securing an anchor in a target area of the skull of a patient, where the anchor has a shaped surface, a top, and a base. In one embodiment, the surgical instrument has a driver with a first end, an opposite second end, and a body portion that is defined between the first end and the second end, which forms a bore inside along a longitudinal axis. The bore is configured to allow the anchor to be received inside it. A first inner surface is formed inside the bore proximate to the first end, and has a shape that is complimentary to the shaped surface of the anchor. An indicator is formed to be received in the bore through the first end, where the indicator has a body, an engaging portion formed in one end of the body for engaging the anchor, and an indicating portion formed in the other end of the body for indicating a position of the anchor during operation.

In one embodiment, the engaging portion is formed with a threaded surface that is complimentary to a corresponding threaded well formed within the anchor. At least one wing portion is formed on an outer surface of the driver. Also, the indicator has a resilient element that is positioned below the indicating portion. At least one protrusion is formed on the second inner surface proximate to the second end of the body portion, for causing a snap fit with the anchor. The indicating portion has a button that extends at least partially above the first end of the driver. In operation, as the driver of the surgical instrument is twisted, the anchor is driven into the skull to a depth at which the base of the anchor is aligned with the second end of the driver and is seated on the surface of the skull, while the button is inside the first end of the driver.

In one embodiment, the indicator has an indicating band with a seating indication mark on its body portion. In operation, as the button is twisted, the anchor is driven into the skull to a depth at which the base of the anchor is aligned with the second end of the driver and is seated on the surface of the skull, while the seating indication mark is aligned with the first end of the driver.

In yet another aspect, the present invention relates to a surgical instrument for securing an anchor in a target area of the skull of a patient, where the anchor has a shaped surface. In one embodiment, the surgical instrument has a driver with a first end and an opposite second end. A body portion is defined between the first end and the second end, and a bore is formed inside the body portion along a longitudinal axis. An indicator is configured to be received in the bore through the first end. The indicator has a body portion, an engaging portion formed in one end for engaging the anchor, and an indicating portion having a button, that is formed in the other end. A receptacle is configured to be received in the bore of the body portion of the driver, proximate to the second end. The receptacle has a first end, a second end, and an inner cavity. A first inner surface is formed inside the inner cavity of the receptacle, proximate to the first end of the receptacle. The first inner surface has a shape that is complimentary to the shaped surface of the anchor. A second inner surface, which has a shape that is different from that of the first inner surface of the receptacle, is also formed inside the inner cavity of the receptacle, between the first inner surface and the second end.

In one embodiment, the shaped surface of the anchor is cross-sectionally hexagonal, the first inner surface of the receptacle is cross-sectionally hexagonal, and the second inner surface of the receptacle is cross-sectionally cylindrical. The engaging portion of the indicator engages with both the receptacle and the anchor, and at least one wing portion is formed on an outer surface of the body portion of the surgical instrument.

In one embodiment, the surgical instrument has a bit with a driving portion and a first outer surface, where the driving portion is formed to be twistably engaged with a powered driving means. A fitting is formed with a dimension to allow the button to be received inside. The fitting has a first end, a second end, and an inner surface formed with a shape that is complimentary to the shape of the outer surface of the bit and the outer surface of the button. The fitting engages with both the bit and the button. A resilient element is positioned below the driving portion of the bit and above the fitting. In operation, as the bit is twisted by the powered driving means, the anchor is driven into the skull to a depth at which the base of the anchor is aligned with the second end of the driver and is seated on the surface of the skull, the top of the anchor is within the first inner surface of the receptacle, and the button is below the second end of the fitting.

In yet another aspect, the present invention relates to a surgical instrument for securing an anchor in a target area of the skull of a patient, where the anchor has a shaped surface, a top, and a base. In one embodiment, the surgical instrument has a driver with a first end, an opposite second end, and a body portion that is defined between the first end and the second end. A bore is formed in the body portion along a longitudinal axis. A receptacle, having a first end, a second end, and an inner cavity, is configured to be received at least in part of the bore, proximate to the second end of the body portion. A first inner surface is formed inside the inner cavity of the receptacle and proximate to its first end, and is formed with a shape that is complimentary to the shaped surface of the anchor. A second inner surface is formed inside the inner cavity of the receptacle, between the first inner surface and the second end of the receptacle, and is formed with a shape that is different from the shape of the first inner surface. The surgical instrument also has a driving mechanism for engaging the receptacle to cause it to move in operation.

In one embodiment, the shaped surface of the anchor is cross-sectionally hexagonal, the first inner surface of the receptacle is cross-sectionally hexagonal, and the second inner surface of the receptacle is cross-sectionally cylindrical. Also, at least one wing portion is formed on an outer surface of the driver. In operation, as the driver is twisted, the anchor is driven into the target area of the skull to a depth at which the base of the anchor is aligned with the second end of the driver and the second end of the receptacle, the base of the anchor is seated on the surface of the skull, and the top of the anchor is within the second inner surface of the receptacle. The driving mechanism of the surgical instrument comprises a top portion, an opposite bottom portion, and a body portion formed between the top portion and bottom portion. The top portion is formed with a shape that is complimentary to the inner surface of the driver, and the body portion of the driving mechanism is formed with a shape that is complimentary to the inner surface of the receptacle. The top portion of the driving mechanism engages with the driver and the body portion of the driving mechanism engages with the receptacle, respectively. A resilient member is positioned below the top portion of the driving mechanism and below the first end of the receptacle. In operation, as a force is applied to the first end of the driver in a direction towards the target area of the skull, the driver is pushed against the resistive force of the resilient member until the bottom portion of the driving mechanism engages the top of the anchor. As the driver is twisted, the anchor is driven into the target area to a depth at which the base of the anchor is aligned with the second end of the driver and the second end of the receptacle, the base of the anchor is seated on the surface of the skull, and the top of the anchor is within the second inner surface of the receptacle.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings in FIGS. 1-5.

Figure 1:
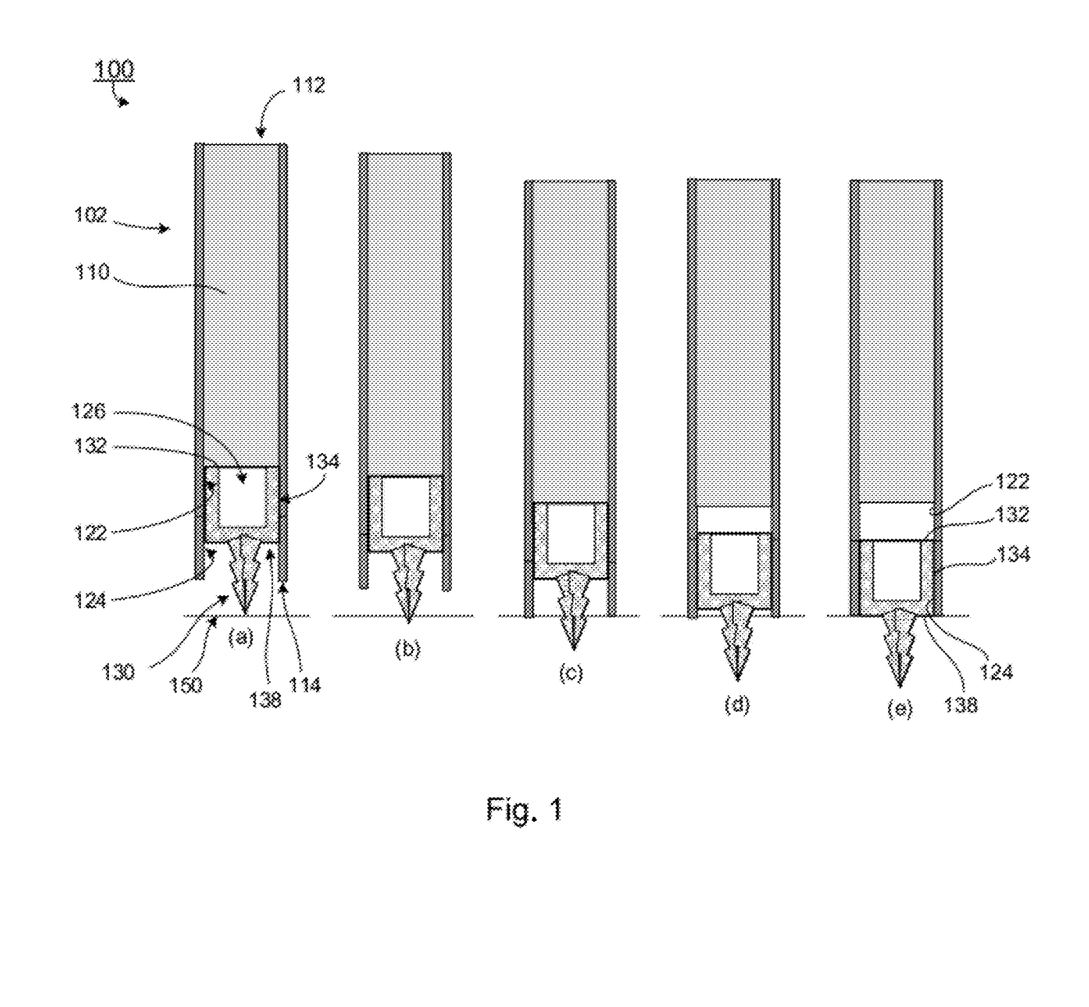
FIG. 1 shows schematically a partial view of a surgical instrument according to one embodiment of the present invention.

Referring now to FIG. 1, the present invention, in one aspect, relates to a surgical instrument 100 for securing an anchor 130 in a target area of the skull 150 of a patient, where the anchor 130 has a shaped surface 134, a top 132, and a base 138. In one embodiment of the present invention as shown, the surgical instrument has a driver 102 with a first end 112, an opposite, second end 114, and a body portion 110 defined between the first end 112 and second end 114. The body portion has a bore 126 inside, along a longitudinal axis, where the bore 126 is configured to allow the anchor 130 to be received inside. A first inner surface 122 is formed inside the bore 126 proximate to the first end 112, with a shape that is complimentary to the shaped surface 134 of the anchor 130. A second inner surface 124, having a shape that is different from the shape of the first inner surface 122, is also formed inside the bore 126, between the first inner surface 122 and the second end 114.

In one embodiment, the shaped surface 134 of the anchor 130 is cross-sectionally hexagonal, the first inner surface 122 is cross-sectionally hexagonal, and the second inner surface 124 is cross-sectionally cylindrical. The first inner surface 122 is dimensioned to engage the shaped surface 134 of the anchor 130, and the second inner surface 124 is dimensioned to allow the anchor 130 to slide inside the bore 126. In operation, as shown in FIG. 1(a-e), as the driver 102 is twisted the anchor 130 is driven into the skull 150 to a depth at which the base 138 of the anchor 130 is aligned with the second end 114 of the driver 102 and is seated on the surface of the skull 150, while the top 132 of the anchor is within the second inner surface 124 of the driver 102, as shown in FIG. 1(e). In one embodiment, the depth is adjustable. At least one of the first inner surface 122 and second inner surface 124 is dimensioned to allow the depth to be adjustable.

As shown in FIG. 1, the surgical instrument 100 has no moving parts. However, a moving indicator may be added, such as that shown in the embodiment of FIG. 5, or some other means of indicating seating, such as by using electrical or optical components, may be provided. As the driver 102 is twisted, as shown in FIG. 1(a), the anchor 130 pulls itself into the skull 150 as it taps a hole, as shown in FIG. 1(b). The anchor 130 descends (see progression shown in FIG. 1(b-d)) to a point (shown in FIG. 1(e)) at which its base 138 is flush with the second end 114 of the driver 102 and the base 138 is against the skull 150, sitting just below the hexagonal first inner surface 122 of the driver 102. At this point, because it is below the first inner surface 122, it is automatically released from the applied torque, which prevents any danger of stripping threads.

Again referring to FIG. 1, as shown the outer surface 134 of the anchor 130 is hexagonal and the second inner surface 124 is cylindrical. When the anchor 130 is located within this portion of the driver 102, the driver 102 cannot exert torque on the anchor 130. The first inner surface 122 is hexagonal such that when the driver 102 is twisted it will exert torque on the anchor 130. The first inner surface 122 does not require an exact hexagonal shape, but it needs to engage the hexagonal outer surface 134 of the anchor 130 in order to exert torque. The driver 102 shown in this exemplary embodiment can be used manually, like a hand-drill, or alternatively it may be driven by a motor that engages the driver at its top or side portions.

Figure 2:
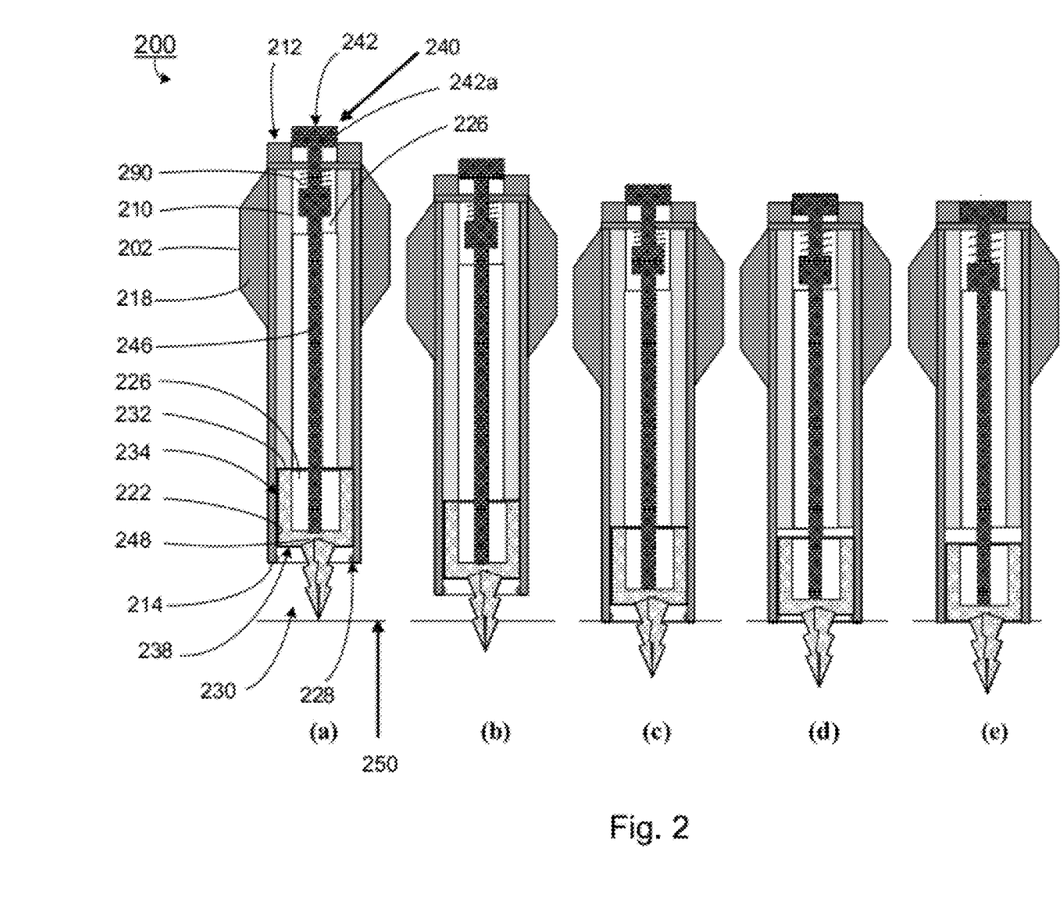
FIG. 2 shows schematically a partial view of a surgical instrument according to another embodiment of the present invention.
Figure 2A:
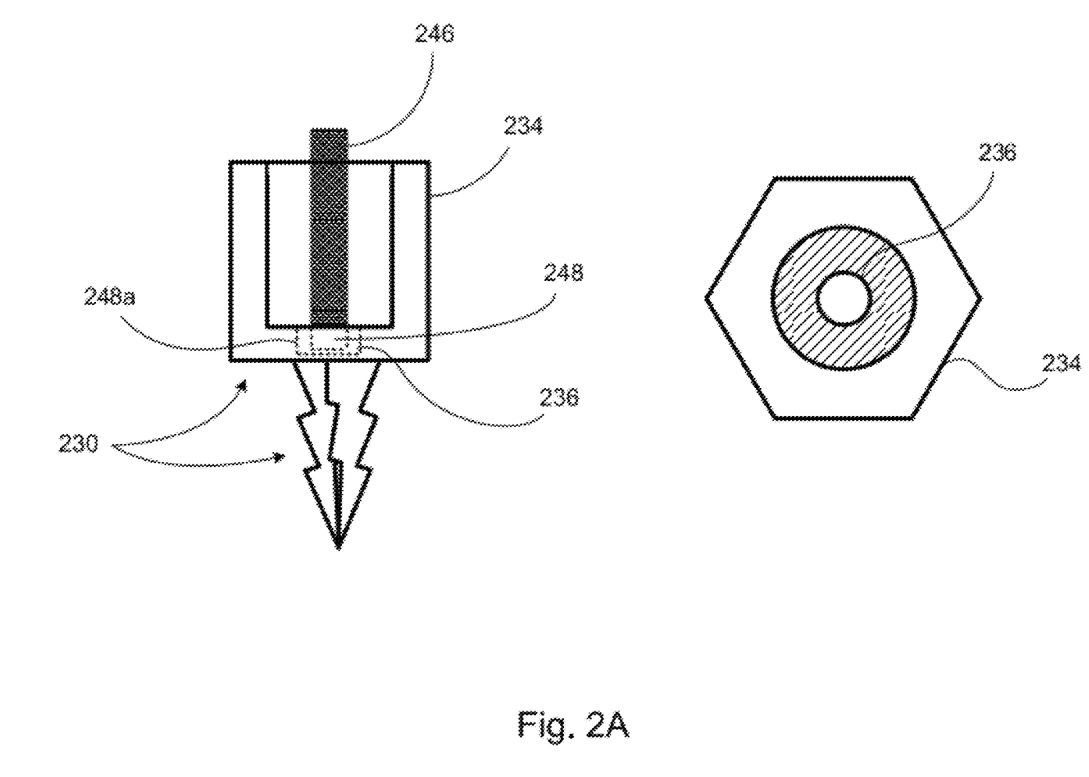
FIG. 2A shows schematically partial views of the indicator and anchor with a threaded well of the surgical instrument according to the embodiment shown in FIG. 2.

Referring now to FIGS. 2 and 2A, in another aspect, the present invention relates to a surgical instrument 200 for securing an anchor 230 in a target area of the skull 250 of a patient, where the anchor 230 has a shaped surface 234, a top 232, and a base 238. In one embodiment as shown, the surgical instrument 200 has a driver 202 with a first end 212, an opposite second end 214, and a body portion 210 that is defined between the first end 212 and the second end 214, which forms a bore 226 inside along a longitudinal axis. The bore 226 is configured to allow the anchor 230 to be received inside it. A first inner surface 222 is formed inside the bore 226 proximate to the second end 214, and has a shape that is complimentary to the shaped surface 234 of the anchor 230. An indicator 240 is formed to be received in the bore 226 through the first end 212, where the indicator 240 has a body 246, an engaging portion 248 formed in one end of the body 246 for engaging the anchor 230, and an indicating portion 242 formed in the other end of the body 246 for indicating a position of the anchor 230 during operation.

In one embodiment, the engaging portion 248 is formed with a threaded surface 248a that is complimentary to a corresponding threaded well 236 formed within the anchor 230. At least one wing portion 218 is formed on an outer surface of the driver 202. Also, the indicator 240 has a resilient element 290 that is positioned below the indicating portion 242. At least one protrusion 228 is formed on the second inner surface 224 proximate to the second end 214 of the body portion 210, for causing a snap fit with the anchor 230. The indicating portion 242 has a button 242a that extends at least partially above the first end 212 of the driver 202. In operation, as the driver 202 of the surgical instrument 200 is twisted, the anchor 230 is driven into the skull 250 to a depth at which the base 238 of the anchor 230 is aligned with the second end 214 of the driver 202 and is seated on the surface of the skull 250, while the button 242a is inside the first end 212 of the driver 202.

Figure 5:
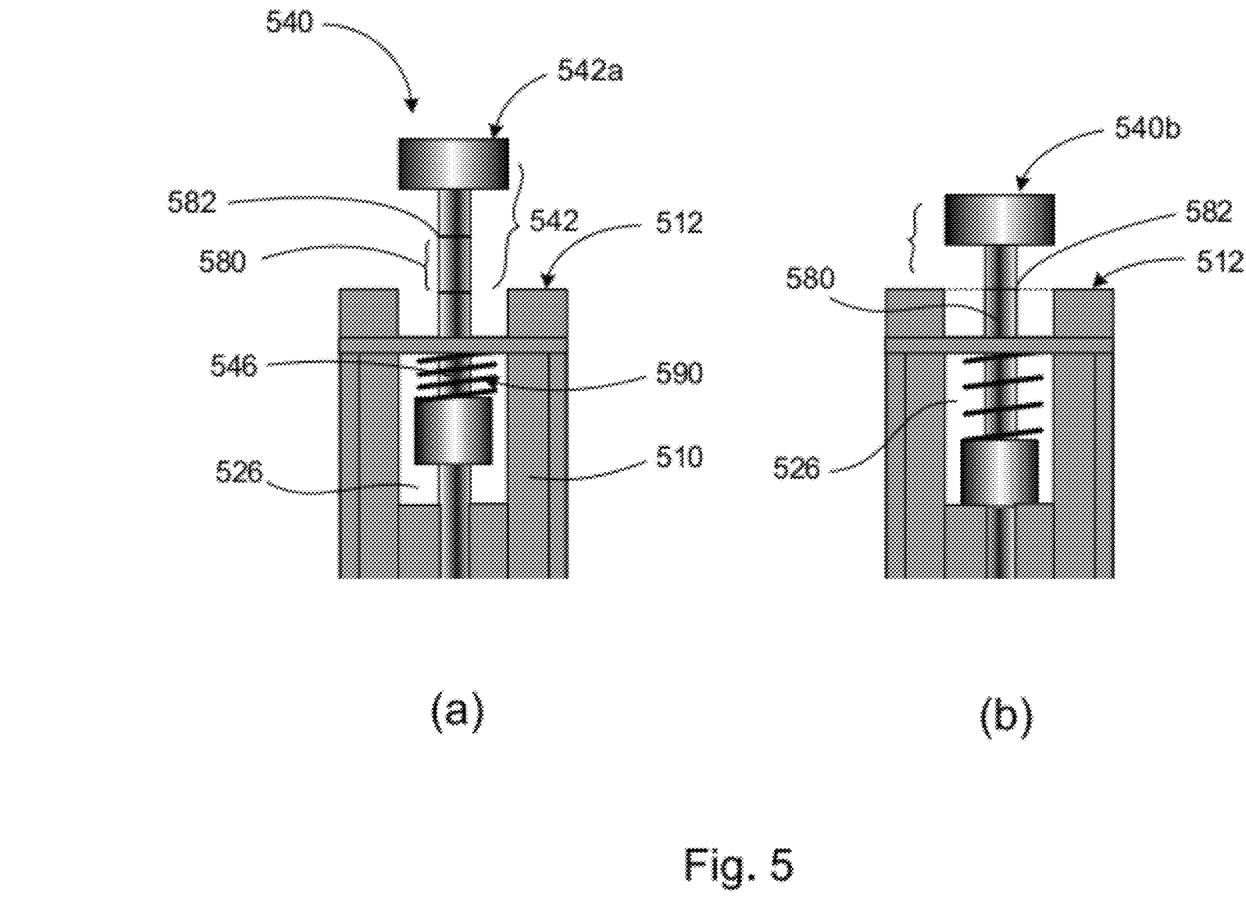
FIG. 5 shows schematically a partial view of a surgical instrument according to yet another embodiment of the present invention.

Referring now to FIGS. 2 and 5, FIG. 5 shows another embodiment of the present invention, in which the indicator 540 has an indicating band 580 with a seating indication mark 582 on its body portion 546. In operation, as the button 542a is twisted, the anchor 230 is driven into the skull 250 to a depth at which the base 238 of the anchor 230 is aligned with the second end 214 of the driver 202 and is seated on the surface of the skull 250, while the seating indication mark 582 is aligned with the first end 512 of the driver 202, at (b).

Figure 3:
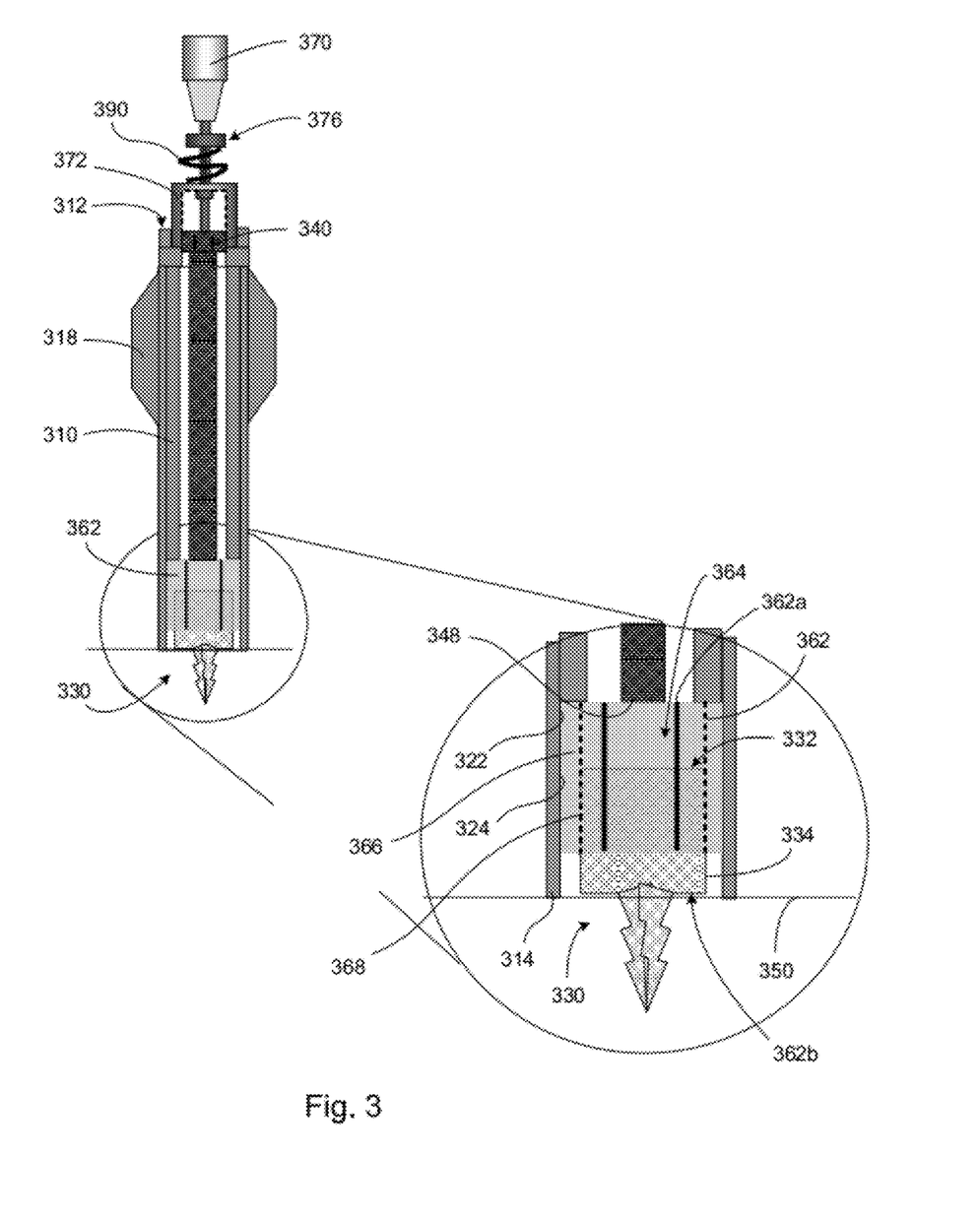
FIG. 3 shows schematically a partial view of a surgical instrument having a driving portion twistably engaged with a powered driving means, according to yet another embodiment of the present invention

Referring now to FIG. 3, in yet another aspect, the present invention relates to a surgical instrument 300 for securing an anchor 330 in a target area of the skull 350 of a patient, where the anchor 330 has a shaped surface 334. In one embodiment as shown, the surgical instrument has a driver 302 with a first end 312 and an opposite second end 314. A body portion 310 is defined between the first end 312 and the second end 314, and a bore 326 is formed inside the body portion 310 along a longitudinal axis. An indicator 340 is configured to be received in the bore 326 through the first end 312. The indicator 340 has a body portion 346, an engaging portion 348 formed in one end for engaging the anchor 330, and an indicating portion 342 having a button 342a, that is formed in the other end. A receptacle 362 is configured to be received in the bore 326 of the body portion 310 of the driver 302, proximate to the second end 314. The receptacle 362 has a first end 362a, a second end 362b, and an inner cavity 364. A first inner surface 366 is formed inside the inner cavity 364 of the receptacle 362, proximate to the first end 362a of the receptacle 362. The first inner surface 366 has a shape that is complimentary to the shaped surface 334 of the anchor 330. A second inner surface 368, which has a shape that is different from that of the first inner surface 366 of the receptacle 362, is also formed inside the inner cavity 364 of the receptacle 362, between the first inner surface 366 and the second end 362b.

In one embodiment, the shaped surface 334 of the anchor 330 is cross-sectionally hexagonal, the first inner surface 366 of the receptacle 362 is cross-sectionally hexagonal, and the second inner surface 368 of the receptacle 362 is cross-sectionally cylindrical. The engaging portion 348 of the indicator 340 engages with both the receptacle 362 and the anchor 330, and at least one wing portion 318 is formed on an outer surface of the body portion 310 of the surgical instrument 300.

Figure 3A:
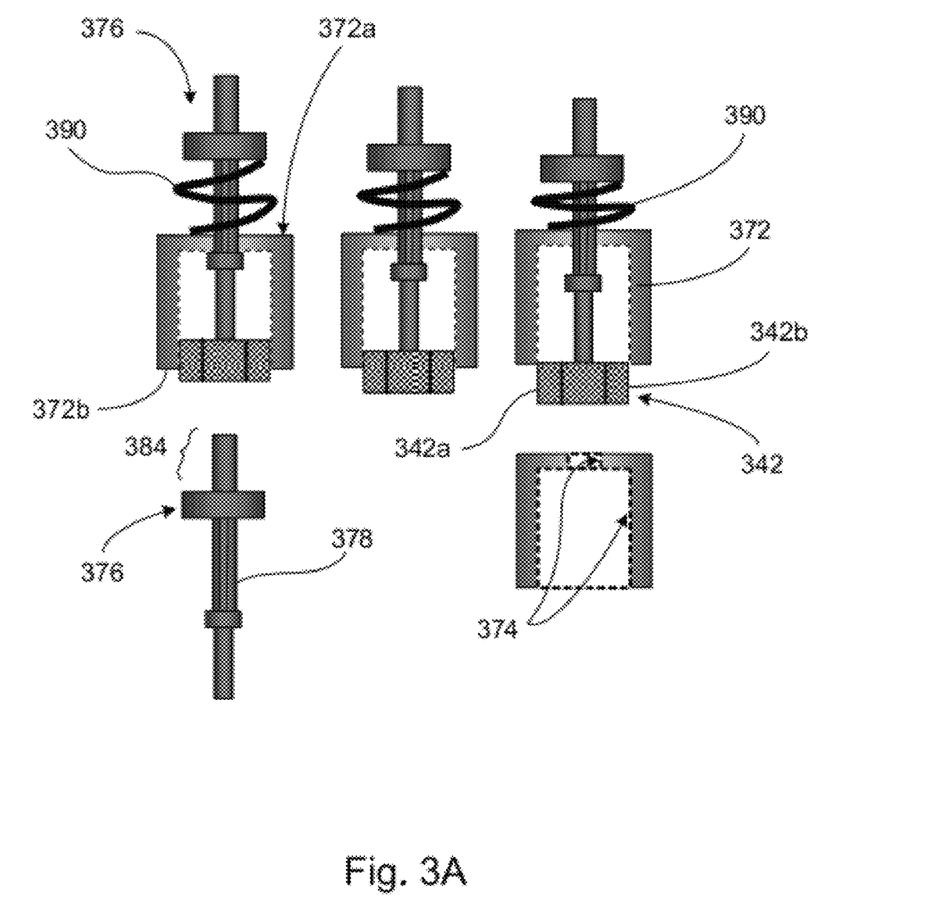
FIG. 3A shows schematically a partial view of a bit and fitting of the surgical instrument according to the embodiment shown in FIG. 3.

In one embodiment, the surgical instrument 300 has a bit 376 with a driving portion 384 and a first outer surface 378, where the driving portion 348 is formed to be twistably engaged with a powered driving means 370. A fitting 372 is formed with a dimension to allow the button 342a to be received inside. The fitting 372 has a first end 372a, a second end 372b, and an inner surface 374 formed with a shape that is complimentary to the shape of the outer surface 378 of the bit 376 and the outer surface of the button 342a. The fitting 372 engages with both the bit 376 and the button 342a, respectively. A resilient element 390 is positioned below the driving portion 384 of the bit 376 and above the fitting 372. In operation, as the bit 376 is twisted by the powered driving means 370, the anchor 330 is driven into the skull 250 to a depth at which the base 138 of the anchor 330 is aligned with the second end 314 of the driver 302 and is seated on the surface of the skull 250, the top 332 of the anchor 330 is within the first inner surface 366 of the receptacle 362, and the button 342 is below the second end 372b of the fitting 372.

Figure 4:
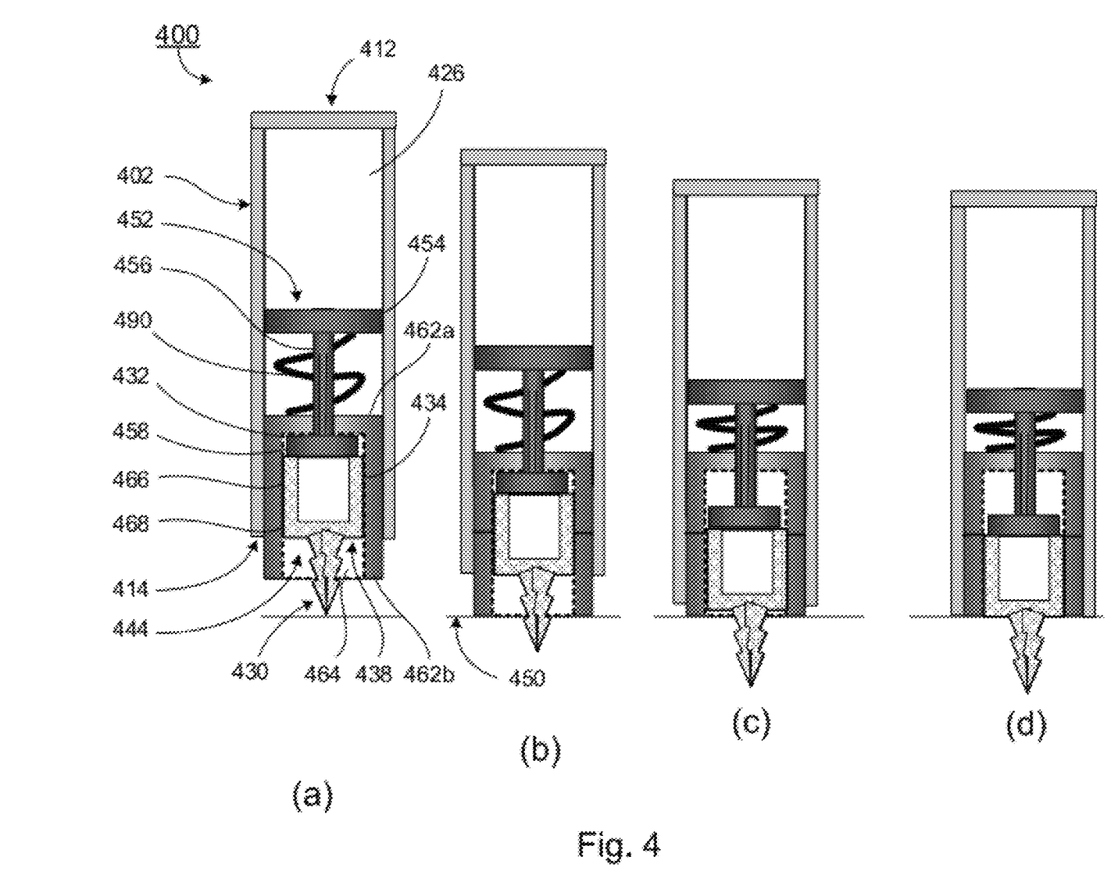
FIG. 4 shows schematically a partial view of a surgical instrument according to yet another embodiment of the present invention.

Referring now to FIG. 4, in yet another aspect, the present invention relates to a surgical instrument 400 for securing an anchor 430 in a target area of the skull 450 of a patient, where the anchor 430 has a shaped surface 434, a top 432, and a base 438. In one embodiment as shown, the surgical instrument has a driver 402 with a first end 412, an opposite second end 414, and a body portion 410 that is defined between the first end 412 and the second end 414. A bore 426 is formed in the body portion 410 along a longitudinal axis. A receptacle 462, having a first end 462a, a second end 462b, and an inner cavity 464, is configured to be received at least in part of the bore 426, proximate to the second end 414 of the body portion 410. A first inner surface 466 is formed inside the inner cavity 464 of the receptacle 462 and proximate to its first end 462a, and is formed with a shape that is complimentary to the shaped surface 434 of the anchor 430. A second inner surface 424 is formed inside the inner cavity 434 of the receptacle 462, between the first inner surface 466 and the second end 462b of the receptacle 462, and is formed with a shape that is different from the shape of the first inner surface 466. The surgical instrument 400 also has a driving mechanism 452 for engaging the receptacle 462 to cause it to move in operation.

In one embodiment, the shaped surface 434 of the anchor 430 is cross-sectionally hexagonal, the first inner surface 466 of the receptacle 462 is cross-sectionally hexagonal, and the second inner surface 468 of the receptacle 462 is cross-sectionally cylindrical. Also, at least one wing portion 418 is formed on an outer surface of the driver 402. In operation, as the driver 402 is twisted, the anchor 430 is driven into the target area of the skull 450 to a depth at which the base 438 of the anchor 430 is aligned with the second end 414 of the driver 402 and the second end 462b of the receptacle 462, the base 438 of the anchor 430 is seated on the surface of the skull 450, and the top 432 of the anchor 430 is within the second inner surface 468 of the receptacle 462. The driving mechanism 452 of the surgical instrument comprises a top portion 454, an opposite bottom portion 458, and a body portion 456 formed between the top portion 454 and bottom portion 458. The top portion 454 is formed with a shape that is complimentary to the inner surface 422 of the driver 402, and the body portion 456 of the driving mechanism 452 is formed with a shape that is complimentary to the inner surface 466 of the receptacle 462. The top portion 454 of the driving mechanism 452 engages with the driver 402 and the body portion 456 of the driving mechanism 452 engages with the receptacle 462, respectively. A resilient member 490 is positioned below the top portion 454 of the driving mechanism 452 and below the first end 462a of the receptacle 462. In operation, as a force is applied to the first end 412 of the driver 402 in a direction towards the target area of the skull 450, the driver 402 is pushed against the resistive force of the resilient member 490 until the bottom portion 458 of the driving mechanism 452 engages the top 432 of the anchor 430. As the driver 402 is twisted, the anchor 430 is driven into the target area of the skull 450 to a depth at which the base 438 of the anchor 430 is aligned with the second end 414 of the driver 402 and the second end 462b of the receptacle 462, the base 438 of the anchor 430 is seated on the surface 468 of the skull 450, and the top 432 of the anchor 430 is within the second inner surface 468 of the receptacle 462.

In another embodiment (not shown), a second release mechanism could be implemented, which would activate in the event that pressure is removed from the anchor. This acts as a failsafe measure for a situation where the user is distracted and does not realize that he or she is turning the anchor without applying sufficient pressure to keep it engaged. In this embodiment, if the user of the surgical instrument did not apply enough pressure to engage the anchor, the driver would merely spin without applying torque. The second release mechanism would comprise a second resilient member configured such that the user would have to overcome its opposing resistive force in order to engage the driver. The resilient member would preferably have the same or higher strength than the first resilient member, such that no torque could be applied without applying pressure to it. Alternatively, instead of using a second resilient member, the upper end of the first resilient member could be used for this purpose.

Figure 6:
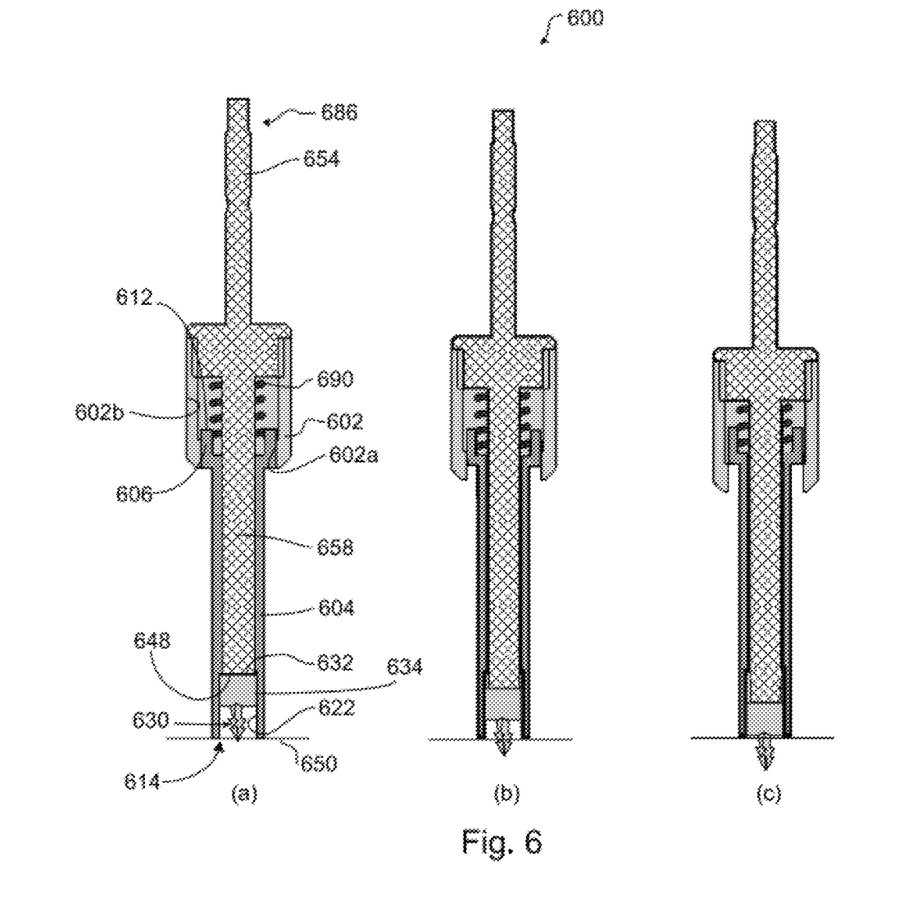
FIG. 6 shows schematically a partial view of a surgical instrument according to yet another embodiment of the present invention.
Figure 6A:
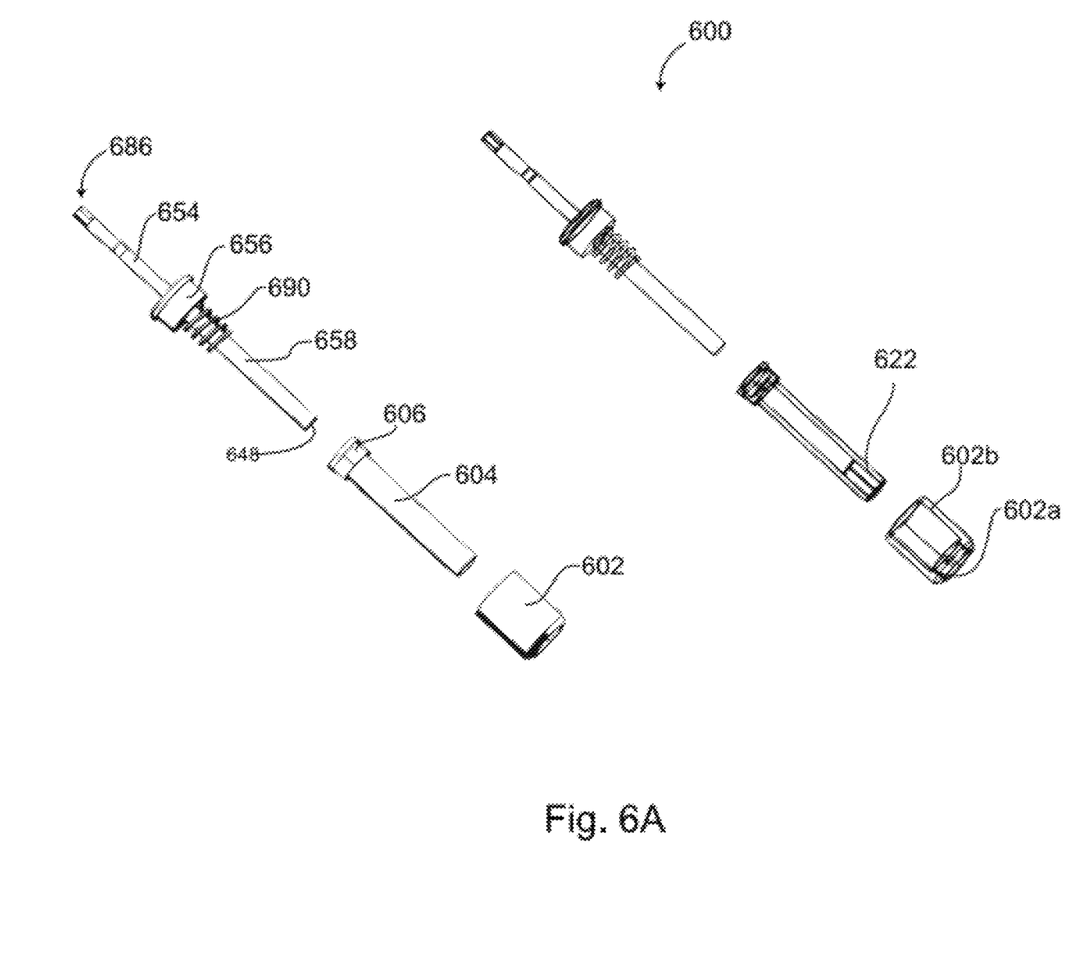

Referring now to FIGS. 6 and 6A, in yet another aspect the present invention relates to a surgical instrument 600 for securing an anchor 630 in a target area of the skull 650 of a patient, where the anchor 630 has a shaped surface. In one embodiment, the surgical instrument 600 has a driver shaft 604, where at one end 614, the driver shaft 604 has a first inner surface 622 which slidably engages with the outer surface 634 of the anchor 630. The cross-sectional shape of the driver shaft 604 prohibits relative rotation between the driver shaft 604 and anchor 630, but allows for relative axial motion. An opposite end 612 of the driver shaft 604 has a top portion 606 of the driver shaft 604, which has an outer surface that slidably engages with the first inner surface 602a of the driver base 602. The shape of the outer surface of the top portion 606 prohibits relative rotation between the driver shaft 604 and driver base 602, but allows for relative axial motion. The height of the top portion 606 of the driver shaft 604 is equivalent to the depth to which the anchor 630 is to be driven. A resilient element 690 is disposed between the driver shaft 604 and driving mechanism 652, which places a force, in a direction towards the anchor 630, on the driver shaft 604 that keeps the driver shaft 604 firmly seated against the skull 650. The driving mechanism 652 has a top portion 686 that is formed to be twistably engaged with a rotationally powered tool, such as a powered driving means as shown in FIG. 3. The body portion 656 of the driving mechanism 652 has threads on its outer surface, external threads which engage the driver base 602. A bottom engaging portion 648 of the driving mechanism 652 engages with and transmits axial force to the anchor 630.

In operation, the engaging portion 686 of the driving mechanism 652 is rotated, such as through the use of a powered driving means (see FIG. 3) that provides a force directed towards the anchor 630, and a rotational force. As the threads of the anchor 630 engage deeper into the skull 650, the anchor 630 moves downward along the vertical axis relative to the driver shaft 604. The driving mechanism 652 moves downward along the vertical axis with the anchor 630 such that, in progression, as shown between steps (a), (b), and (c) of FIG. 6, less and less of the outer surface of the top portion 606 of the driver shaft 604 is engaged, as the anchor 630 is driven further into the skull 650. As shown at step (c), at the point at which the hexagonal portion on the top portion 606 of the driver shaft 604 are no longer in contact and the driver shaft 604 is no longer rotationally engaged with the first inner surface 602a of the driver base 602, the anchor is seated against the skull 650 at the correct depth. As such, the driver shaft 604 is then stationary, as is the anchor 630, although the driving mechanism 652 and driver base 602 may still be rotating.

In one embodiment, the depth to which the anchor 630 is to be driven is adjustable, and at least one of the first inner surface 602a of the driver base 602 and the outer surface portion of the top portion 606 of the driver shaft 604 is dimensioned to allow the depth to be adjustable.

In one embodiment, the engaging surfaces of the driver shaft 604, driver base 602, and driving mechanism 652 are hexagonal. However, these surfaces are not limited as such and could be formed as another geometric shape that allows relative axial motion while transmitting rotational motion. Further, the device of this embodiment is not limited to driving an anchor 630. Any threaded fastener which is itself screwed into the skull 650, or is used as a fastener to hold another component in place, can be used in conjunction with this embodiment of the present invention.

Surgical instruments of various embodiments of the present invention can be made with different sizes or dimensions, and with proper materials such as metallic materials, plastic materials, wood materials, combinations of them, or the like.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A surgical instrument for securing an anchor in a target area of the skull of a living subject, wherein the anchor has a shaped surface, comprising:
   (a) a driver having a first end, an opposite, second end, and a body portion defined therebetween forming a bore therein along a longitudinal axis;
   (b) an indicator configured to be received in the bore through the first end, wherein the indicator has a body portion, an engaging portion formed in one end of the body portion of the indicator for engaging the anchor, and an indicating portion formed in the other end of the body portion of the indicator and having a button;
   (c) a receptacle configured to be received in the bore of the body portion of the driver and proximate to the second end of the body portion, wherein the receptacle has a first end, a second end and an inner cavity defined therein;
   (d) a first inner surface formed inside the inner cavity of the receptacle and proximate to the first end of the receptacle;
   (e) a second inner surface formed inside the inner cavity of the receptacle and between the first inner surface and the second end of the receptacle, wherein the second inner surface of the receptacle is formed with a shape that is different from that of the first inner surface of the receptacle,
   (f) a bit having a driving portion and a first outer surface, wherein the driving portion is formed to be twistably engaged with a powered driving means;
   (g) a fitting formed with a dimension to allow the button to be received therein, having a first end, a second end, and an inner surface formed with a shape that is complimentary to the shape of the outer surface of the bit and complimentary to the outer surface of the button, and wherein the fitting engages with both the bit and the button; and
   (h) a resilient element positioned below the driving portion of the bit and above the fitting.

2. The surgical instrument of claim 1, wherein the first inner surface of the receptacle is cross-sectionally hexagonal.

3. The surgical instrument of claim 1, wherein the second inner surface of the receptacle is cross-sectionally cylindrical.

4. The surgical instrument of claim 1, wherein the engaging portion of the indicator engages with both the receptacle and the anchor.

5. The surgical instrument of claim 1, further comprising at least one wing portion formed on an outer surface of the body portion of the surgical instrument.

6. The surgical instrument of claim 1, wherein in operation, as the bit is twisted by the powered driving means, the anchor is driven into the skull to a depth at which the base of the anchor is aligned with the second end of the driver and seated on the surface of the skull, the top of the anchor is within the first inner surface of the receptacle, and the button is below the second end of the fitting.

* * * * *